United States Patent
West et al.

(10) Patent No.: US 7,556,042 B2
(45) Date of Patent: Jul. 7, 2009

(54) METHODS AND SYSTEMS FOR TRACHEAL ACCESS AND VENTILATION

(75) Inventors: Scott H. West, Livermore, CA (US); Amir Abolfathi, Woodside, CA (US); Christopher Lolachi, Palo Verdes, CA (US)

(73) Assignee: APMed Solutions, Inc., Woodside, CA (US)

( * ) Notice: Subject to any disclaimer, the term of this patent is extended or adjusted under 35 U.S.C. 154(b) by 633 days.

(21) Appl. No.: 11/132,603

(22) Filed: May 18, 2005

(65) Prior Publication Data

US 2006/0260616 A1    Nov. 23, 2006

(51) Int. Cl.
*A61M 16/00* (2006.01)
*A62B 9/06* (2006.01)
*A62B 9/02* (2006.01)

(52) U.S. Cl. ............... 128/207.16; 128/207.14

(58) Field of Classification Search ............ 128/200.26, 128/207.14, 207.15, 207.16, 207.29; 606/108; 604/264, 506, 174
See application file for complete search history.

(56) References Cited

U.S. PATENT DOCUMENTS

| | | | | |
|---|---|---|---|---|
| 3,263,684 A * | 8/1966 | Bolton | ................... | 128/207.16 |
| 4,246,897 A * | 1/1981 | Muto | ................... | 128/207.15 |
| 4,278,081 A | 7/1981 | Jones | | |
| 4,280,492 A | 7/1981 | Latham | | |
| 4,305,392 A | 12/1981 | Chester | | |
| 4,488,545 A * | 12/1984 | Shen | ................... | 128/207.29 |
| 4,794,924 A * | 1/1989 | Eliachar | ................... | 128/207.16 |
| 4,840,173 A | 6/1989 | Porter, III | | |
| 4,979,505 A | 12/1990 | Cox | | |
| 5,054,484 A | 10/1991 | Hebeler, Jr. | | |
| 5,056,515 A | 10/1991 | Abel | | |
| 5,067,497 A | 11/1991 | Greear et al. | | |
| 5,107,828 A | 4/1992 | Koss et al. | | |
| 5,143,062 A | 9/1992 | Peckham | | |
| 5,250,025 A * | 10/1993 | Sosnowski et al. | .......... | 604/506 |
| 5,311,864 A | 5/1994 | Huerta | | |
| 5,392,775 A | 2/1995 | Adkins, Jr. et al. | | |
| 5,494,029 A * | 2/1996 | Lane et al. | ............. | 128/207.15 |
| 5,501,215 A | 3/1996 | Huerta | | |
| 5,653,231 A | 8/1997 | Bell | | |
| 5,957,978 A | 9/1999 | Blom | | |
| 6,109,264 A * | 8/2000 | Sauer | ..................... | 128/207.29 |
| 6,460,540 B1 | 10/2002 | Klepper | | |
| 6,575,944 B1 | 6/2003 | McNary et al. | | |
| 6,612,305 B2 | 9/2003 | Fauza | | |

(Continued)

*Primary Examiner*—Justine R Yu
*Assistant Examiner*—Kristen C Matter
(74) *Attorney, Agent, or Firm*—Townsend and Townsend and Crew LLP

(57) ABSTRACT

A tracheostomy is performed using an access device and a separate ventilation device. The access device is introduced through a surgical opening in the tracheal wall and has an anchor which is expanded in situ to hold the access device in place. The ventilation device is introduced through a passage in the access device and has an expandable cuff which is oriented above the access point through the tracheal wall. A concavity in the expandable cuff collects body secretions, and other materials from the oral and nasal cavities and/or gastrointestinal reflux into the trachea, and the collected secretions are removed by aspiration through a lumen provided in the ventilation device. A one-way valve may be provided in the expandable cuff in order to permit exhalation through the larynx to assist in speech.

36 Claims, 17 Drawing Sheets

U.S. PATENT DOCUMENTS

| | | |
|---|---|---|
| 6,840,242 B1 | 1/2005 | McCoy |
| 6,843,250 B2 | 1/2005 | Efrati |
| 6,958,044 B2 * | 10/2005 | Burbank et al. ............. 600/564 |
| 7,021,314 B1 * | 4/2006 | Lane ..................... 128/207.29 |
| 7,300,448 B2 * | 11/2007 | Criscuolo et al. ........... 606/190 |
| 2003/0037789 A1 | 2/2003 | Klinberg et al. |

* cited by examiner

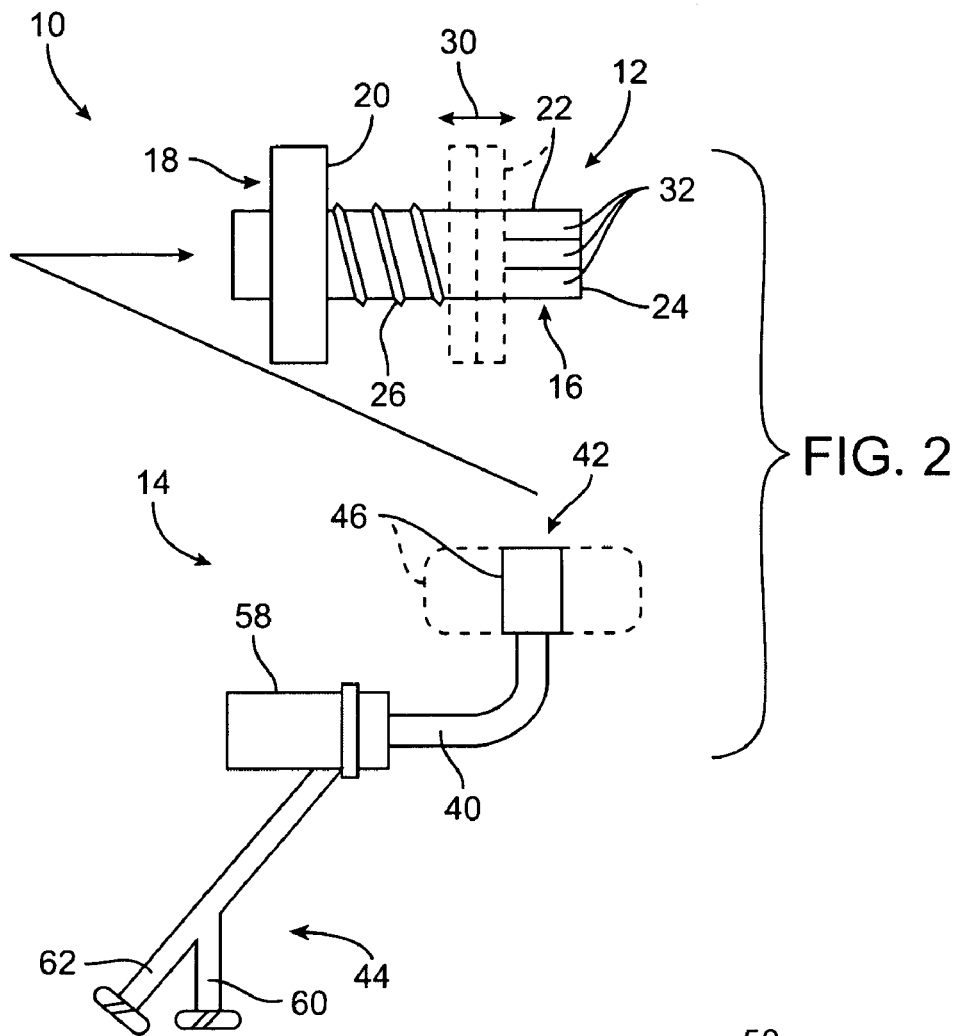
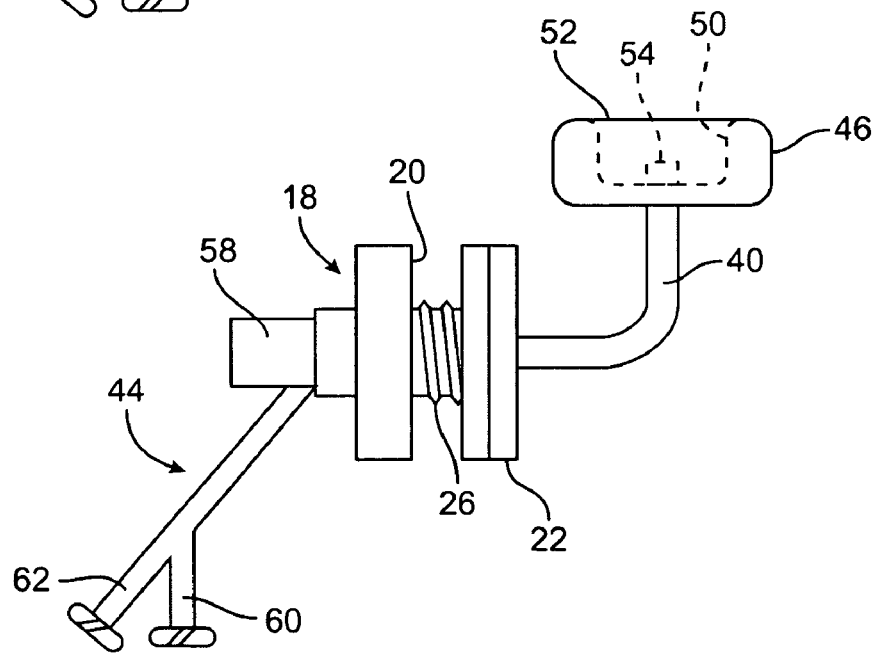
FIG. 3

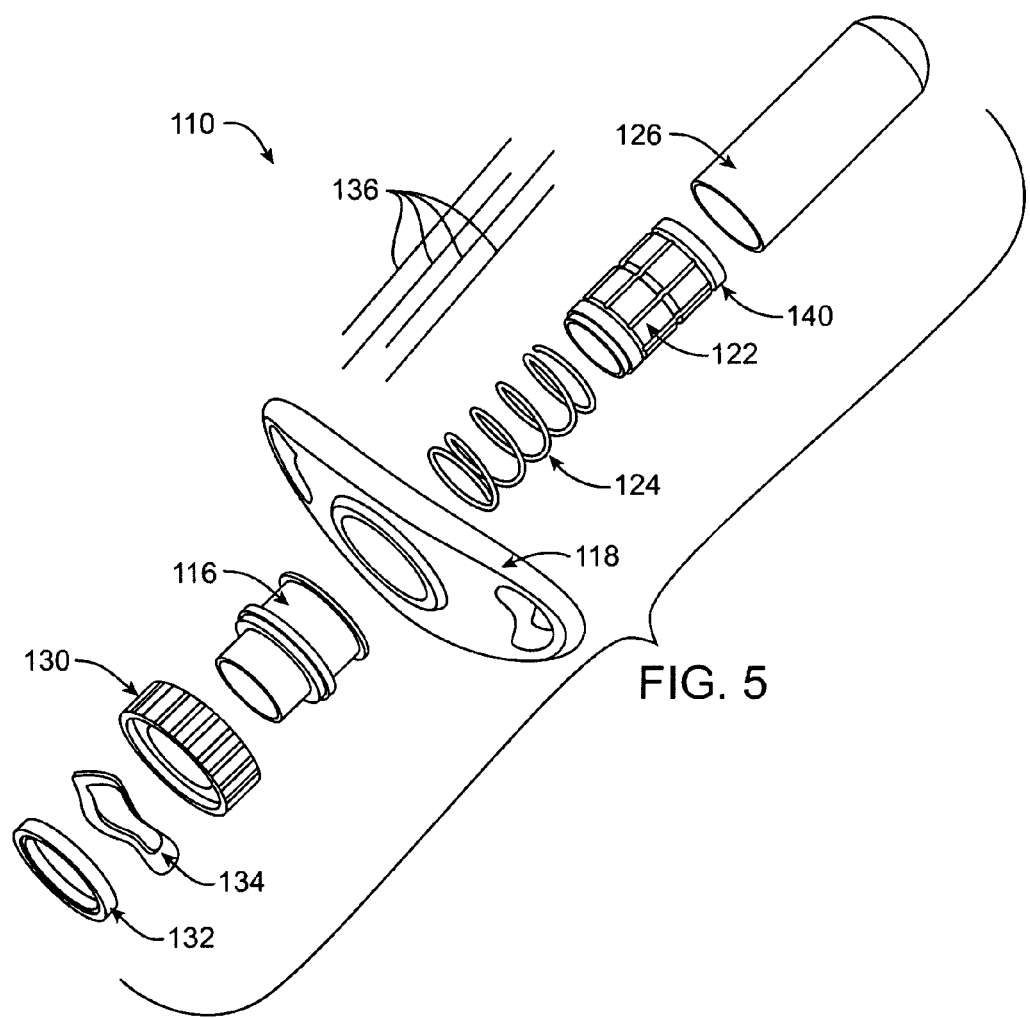

METHODS AND SYSTEMS FOR TRACHEAL ACCESS AND VENTILATION

BACKGROUND OF THE INVENTION

1. Field of the Invention

The present invention relates generally to medical apparatus and methods. More particularly, the present application relates to apparatus, systems, and methods for airway management using a tracheostomy tube. The invention also relates to a transcutaneous access device useful for placing a tracheostomy device or other medical apparatus.

A tracheostomy is a surgical procedure to form an opening into a patient's trachea (windpipe) to provide a temporary or permanent path for ventilation. Usually, a tube is inserted through the opening to allow passage of air and optionally removal of secretions. Instead of breathing through the nose and the mouth, the patient will breath directly through the "tracheal tube." Tracheostomies are often performed in the event of respiratory failure and/or upper airway blockage, and the tracheal tubes may be connected to mechanical ventilators when the patient is unable to breathe on his or her own.

Tracheal tubes may be simple tubes which are bent downward into the trachea to provide the lumen passageway for inhalation and exhalation. Often, however, the tracheal tube will have an inflatable cuff at its lower end in order to provide an airtight system for mechanical ventilation.

Of particular interest to the present invention, tracheal tubes with an inflatable cuff may collect body secretions and other materials from oral cavities, nasal cavities and/or gastro-intestinal reflux into the trachea, which may travel down the trachea from reaching the lungs. Often, these secretions and other materials collect or pool on top of the inflated cuff, thus requiring periodic removal. Even with the cuff inflated, due to movement of the tracheostomy tube and the collection of the materials on top, there could be slow and continuous of the secretions around the cuff. Whenever the cuff is deflated, the secretions remaining on top of the cuff will flow downward into the lung, leading to significant complications. For example, exposure of the lungs to such secretions can cause "aspiration pneumonia" and other pathological conditions, which can have serious consequences and which can prolong and complicate a hospitalization and or even lead to death.

In addition to collection of nasal and other secretions, presently designed tracheal tubes have a number of other shortcomings. For example, many tracheal tubes are difficult to introduce and deploy through penetrations made in the tracheal wall. It can be even more difficult to remove and exchange tracheal tubes for cleaning, repair, or other purposes. Additionally, the inflatable cuffs on at least most trach tubes will be positioned below the tracheal penetration which can be disadvantageous in several respects. The device can be accidentally dislodged when attaching or removing other respiratory devices to the trach tube. In addition, the forces caused by airway irritation may cause the expulsion or dislodgment of the trach tube. Since these patients are dependent on mechanical ventilation, expulsion and dislodgment of the trach tube can cause significant morbidity. Furthermore, by placement of the cuff below the access site, the fluid collected above the cuff balloon can expose the tissue on the access site. Since these secretions are often rich in enzymes, it can lead to break down of the exposed tissue at the access site by the amylase of saliva. The degeneration of the exposed tissue by these enzymes is a well documented in clinical journals and is one of the leading causes of continuous enlargement of the access site for patients with chronic need for trach tube.

For these reasons, it would be desirable to provide improved tracheal tube designs and methods for their deployment and use. It would be particularly useful to provide tracheal tubes which allow for efficient and continuous removal of secretions without the need for separately accessing the tracheal tubes or removing any components of the tracheal tubes. It would be further desirable if the tracheal tubes were designed to permit easy introduction and removal of the tracheal tubes, thus permitting removal and exchange of tracheal tubes with minimum trauma to the patient. To that end, it would be desirable to provide access devices for penetrating the tracheal wall and providing an access port for insertion, removal, and replacement of the tracheal tube, particularly where the access device could be useful for other percutaneous access protocols. It would be still further desirable if the tracheal tubes were able to be firmly anchored in place within the tracheal penetration while causing minimal trauma and irritation to the patient. It is still further desirable that, with the tracheal tube in place, the penetration through the tracheal wall will be effectively sealed to prevent fluid and food aspiration into the lungs. Still further, it would be desirable to provide a tracheal tube which would facilitate patient speech while the tracheal tube is in place. At least some of these objectives will be met by the inventions described herein below.

2. Description of the Background Art

U.S. Pat. No. 6,840,242 describes a tracheostomy aspiration suction tube for use with or without a tracheostomy cuff. Other tracheostomy tubes are described in U.S. Pat. Nos. 6,612,305; 6,575,944; 6,460,540; 5,957,978; 5,653,231; 5,392,775; 5,107,828; 5,056,515; 5,054,484; 4,979,505; 4,280,492; 4,278,081; and published U.S. application 2003/0037789. Certain endotracheal tubes are described in U.S. Pat. Nos. 6,843,250; 5,501,215; 5,311,864; 5,143,062; 5,067,497; 4,840,173; and 4,305,392.

BRIEF SUMMARY OF THE INVENTION

The present invention provides systems, devices, and methods for the improved deployment and maintenance of tracheal tubes for ventilating patients through tracheostomies. The systems of the present invention will usually comprise a percutaneous access device located in the tracheostomy and a separate ventilation tube which can be removably introduced through a passage provided by the access device. The access device is capable of being firmly but atraumatically anchored in the tracheostomy opening, thus facilitating introduction, maintenance, removal, and replacement of the ventilation tube, with minimum patient trauma. Such facilitated replacement and removal of the ventilation tubes greatly improves the ability to clean, repair, and replace the ventilation tubes, which is a particular advantage for patients being ventilated over relatively lengthy periods.

The ventilation tubes themselves are also improved in a number of respects. For example, the endotracheal tubes are adapted to provide for efficient aspiration and removal of secretions and other materials released from the oral and nasal cavities or from gastro-intestinal reflux into the trachea. The secretions are collected on a structure which is positioned above the tracheal penetration and which may be continuously aspirated with either an active suction source or passively via gravitational force to remove secretions and other materials collecting on top of the cuff. The structure, typically in the form of a cup, is preferably valved in a way to facilitate passage of air from the lungs to the larynx in order to facilitate speech, and the cuff may be hinged to facilitate introduction and removal of the tube through the access device. In addition, a separate ventilation fitting may be provided to help seal the ventilation tube within the access device and to permit connection of the patient to a conventional ventilation system.

In a first specific aspect of the present invention, a percutaneous access device is provided which is useful for anchoring within a penetration in the patient's trachea. Although described with particularity for use in the trachea, it will be appreciated that the percutaneous access device may be used to provide other percutaneous access routes, including to the abdomen, thorax, intestines, and other body cavities and lumens. In particular, the access devices may be used in procedures including gastrostomies, colonostomies, ileostomies, laparoscopies, vascular access, and the like.

Percutaneous access devices according to the present invention will usually comprise a base, a conduit having an access lumen, and an anchor. The base will have a posterior surface adapted to cover a percutaneous tissue penetration, and the conduit will be disposed through the base, typically being oriented at a generally perpendicular angle, and be adapted to pass through the tissue penetration. The anchor is located on a posterior portion of the conduit and is shiftable between an unexpanded deployment configuration and an expanded anchoring configuration. Usually, a compliant connector is provided between the base and the anchor to accommodate differences in the thickness of the tissue penetration. Conveniently, the compliant connector may comprise a coil spring, an accordion structure, or the like.

The anchor may comprise a variety of expandable mechanisms capable of being expanded in situ to effect anchoring of the base and conduit. For example, the anchor may comprise a mechanically expandable structure, such as a malecot, a deformable braid, deployable hooks, elongated coil, or the like. Alternatively, the anchor may comprise an inflatable structure, such as a toroidal balloon or other similar geometry. In all cases, the anchor will act to capture tissue circumscribing the tissue penetration between the base and an anterior surface of the anchor. The anterior surface of the anchor will often be tensioned or pressured against a posterior surface of the tissue by the compliant connector as described in more detail below.

In a particular embodiment, the anchor comprises an anchor element which radially expands upon axial compression, typically being a malecot or an expandable braid. The anchor is secured to the base by a compliable mount, such as a coil spring, and a pulling assembly is connected between the anchor element and the base in order to both radially expand the anchor element and to pull the radially expanded anchor element against the posterior tissue surface. Often, the pulling assembly comprises a reel and one or more tethers between the reel and the anchor. Alternatively, the pulling assembly could comprise a pair of coaxial tubes for both opening the anchor and translating the anchor against the posterior tissue surface. In a still further embodiment, the pulling assembly may comprise a locking clip and a pull tool for capturing and pulling a posterior end of the anchor toward the base.

In a further aspect of the present invention, percutaneous access through skin is provided by first penetrating the skin to provide an access hole. A conduit is passed through the hole so that a posterior end of a base on the conduit covers the access hole. An anchor on the conduit is then expanded over a posterior surface of the skin to hold the conduit in place. Typically, the skin is in the neck, chest, or abdomen, most typically being in the neck in order to perform a tracheostomy. Penetrating typically comprises forming an incision or puncture, and the anchor may be expanded by mechanically expanding a structure, such as a malecot, deformable braid, or hooks, or by inflating an inflatable structure. Preferably, the methods further comprise adjusting the distance between the expanded anchor and the posterior surface of the base to accommodate the variable wall thickness. For example, adjusting may comprise tensioning a compliant member between the anchor and the base.

In a further aspect of the present invention, a tracheal ventilation device comprises a tube having a distal end, a proximal end, and an aspiration lumen therethrough. An expandable cuff is disposed at a distal end of the tube, and the cuff has an expandable periphery which can seal against an inner tracheal wall. The cuff further has an upper surface adapted to collect and pool nasal and other secretions, and the aspiration lumen of the tube is coupled to aspirate pooled secretions. A portion of the tube will be upwardly bent or bendable so that the cuff will be disposed above an axis of the tube when deployed in the trachea. In this way, the secretions pooling on the upper surface of the expandable cuff are maintained above the opening. This will prevent or minimize the exposure of these secretions rich in enzymes to the tissues surrounding the access site. As a result limited or no degeneration of the tissues is expected. By having the expandable cuff above the opening there is no risk of device dislodgment or expulsion caused by airway irritation since the exhalation port is positioned below the cuff. Furthermore, the design does not need external securing device such sutures or trach ties since the design allows for the flow of airway pressures in such manner to make the device more stable with patient coughing rather than expulsion that is seen in current trach tubes designs. Suction of the aspiration material in this design can be gravity dependent rather than the need for anti-gravity suctioning that is done with the current devices.

In yet another aspect of the present invention, a tracheal ventilation device may comprise a tube and an expandable cuff, as generally set forth above. The tracheal ventilation device will further comprise a one-way valve in the cuff to permit air from the lungs to pass upwardly into the larynx when the cuff is expanded in the trachea.

In still another aspect of the present invention, a tracheal ventilation device may comprise a tube and an expanded cuff, as just described. The ventilation device will further comprise a ventilation fitting having an end adapted to removably mount in the tracheal access device, a second end adapted to removably connect to a ventilator, and a passage therethrough to receive the ventilation tube. For each of these three tracheal ventilation devices, the ventilation tube will typically include at least a second lumen for ventilation, and will more usually include at least a third lumen for inflating an inflatable expandable cuff. The second lumen may be connected to a one-way valve in the cuff that permits airflow to the larynx (to facilitate speech), and the tube will typically be hinged to allow axial alignment of the tube during deployment and subsequent upward orientation of the cuff after entry of the tube into the trachea. The upper surface of the expandable cuff will typically have a concave region for collecting and pooling nasal and other secretions, typically being a conical concavity. The expandable cuff may be either inflatable or self-expanding.

In yet another aspect of the present invention, a tracheal ventilation system comprises a tracheal access device adapted to anchor in a hole in the trachea and provide an access passage therethrough and a tracheal ventilation device adapted to be removably secured in the tracheal access device. The tracheal access device preferably comprises a base, a conduit, and an anchor, as generally described above. The tracheal ventilation device typically comprises a tube and an expandable device, also as generally described above.

In still further aspects of the present invention, methods for providing tracheal ventilation comprise forming a percutaneous hole into a patient's trachea. A tracheal ventilation device is introduced through the hole, and a cuff on the ventilation device expanded to isolate the trachea below the cuff. The trachea below the cuff is otherwise unblocked to permit air exchange through the ventilation device, and nasal secretions which collect on an upper surface of the cuff may be aspirated. Usually, the cuff is expanded within the trachea at a position above the percutaneous hole, and the pooled secretions are collected in a concavity in the upper surface of the cuff. Usually, the secretions are aspirated from the concavity through a vertical passage through the expanded cuff, and in all cases, the tracheal ventilation device is preferably held in an access device which is anchored in the percutaneous hole.

In yet another aspect of the present invention, a method for providing tracheal ventilation comprises forming a percutaneous hole in a patient's trachea, anchoring an access device in the percutaneous hole, and removably introducing a tracheal ventilation device through an access passage of the access device. Usually, a cuff will be expanded on the tracheal ventilation device, preferably at a location in the trachea above the tracheal penetration. Usually, the trachea below the expanded cuff will remain otherwise unblocked to permit air exchange through the ventilation device. The method will typically further comprise aspirating collected nasal and other secretions from a collection location on an upper surface of the cuff, and the cuff will be removably introduced through a ventilation fitting in the access passage of the access device.

BRIEF DESCRIPTION OF THE DRAWINGS

FIG. 2 is a schematic illustration of a system according to the present invention comprising an access device and a tracheal ventilation device.

FIG. 3 is a schematic illustration of the system of FIG. 2, shown with the tracheal ventilation device in place within a passage of the access device.

FIG. 5 illustrates a first specific embodiment of an access device constructed in accordance with the principles of the present invention.

DETAILED DESCRIPTION OF THE INVENTION

The present invention is intended primarily to provide tracheal access to patients for ventilation, drug delivery, and other therapeutic purposes. To that end, the present invention relies on an access device which anchors in a surgical hole formed in the trachea to provide an access passage and a ventilation device which is removably deployable through the access passage. Although illustrated hereinafter for use in tracheal access protocols, the access device of the present invention is also useful for accessing other body lumens and cavities, such as the stomach, intestines, abdominal cavity, and the like, and for performing procedures such as laparoscopy, gastroscopy, feeding tube deployment, colostomies, ileostomies, and the like.

Figure 1:
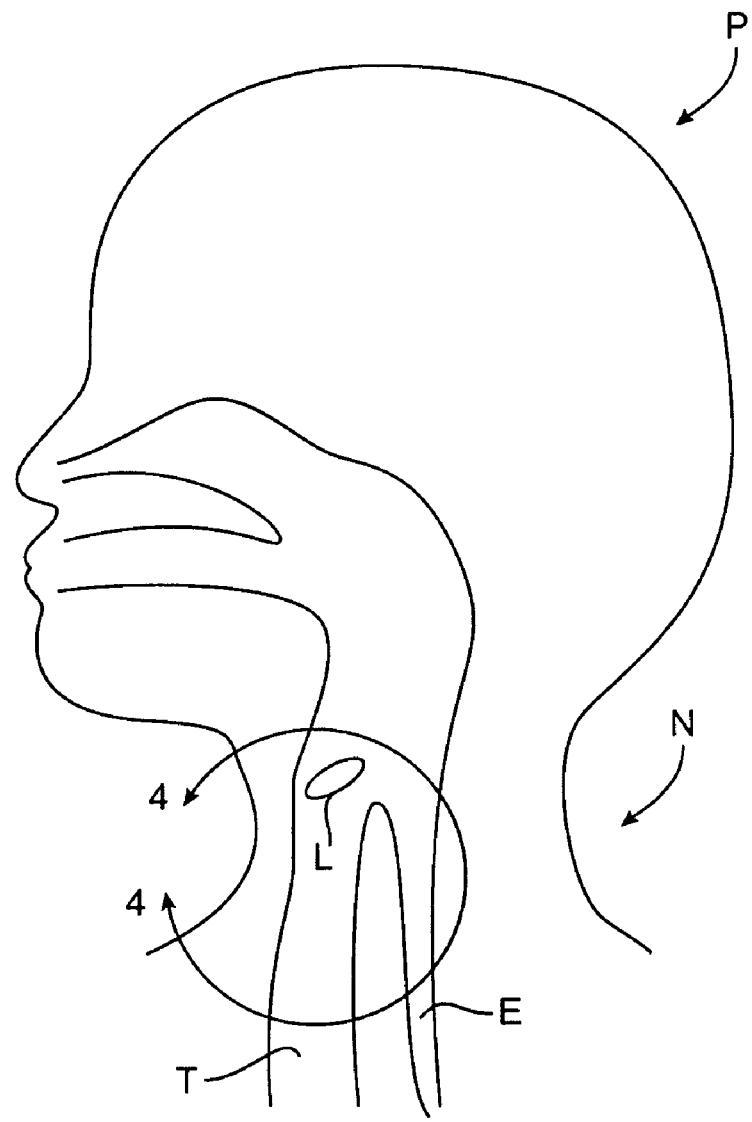
FIG. 1 illustrates the relationship between the trachea and the esophagus in the neck of a patient.

Referring now to FIG. 1, a neck region N of a patient P includes both the esophagus E for passing food and drink to the stomach and the trachea T for exchanging air with the lungs. The larynx L is located generally above the trachea, and incisions into the trachea to perform tracheostomies are generally made well below the larynx, as described in more detail below with reference to FIGS. 4A-4F.

Systems 10 according to the present invention generally comprise an access device 12 and a ventilation device 14. The access device comprises a conduit 16, which may be a single component or an assembly of a plurality of components, which is secured through a base 18 having a posterior surface 20 adapted to cover a percutaneous tissue penetration, such as a tracheal penetration of the type formed when performing a tracheostomy. An anchor structure 22 is disposed at or near a posterior end 24 of the conduit 16. The anchor structure is shiftable or deployable between a low-profile configuration (shown in full line in FIG. 2) and a radially expanded, deployed configuration (shown in broken line in FIG. 2 and full line in FIG. 3). A spring 26 or other compliant member is provided between the anchor structure 22 and the base 18 in order to permit the anchor 22 to move axially relative to the base 20, as indicated by arrow 30 in FIG. 2. As illustrated in FIG. 2, the anchor structure 22 is a malecot having a plurality of individual arms 32 which will radially expand as the malecot is foreshortened, typically by a pulling assembly (not shown in FIGS. 2 and 3).

The ventilation device 14 comprises a tube 40 having a distal end 42 and a proximal end 44. An expandable cuff 46 is mounted at or near the distal end 42 of the tube 40 and may be inflated from the low-profile configuration shown in full line to a radially expanded configuration shown in broken line in FIG. 2. In addition to inflatable structures, the expandable cuff 46 may also comprise self-expanding structures, such as a self-expanding cone formed from resilient polymer or other materials. A cavity 50 (shown in broken line in FIG. 3), is usually formed in an upper surface 52 of the expanded cuff 46 in order to collect nasal and other secretions after the cuff is deployed in the trachea. A valve structure 54 is disposed within the cavity 50 and typically serves two purposes. First, the valve will contain a port for aspirating the collected secretions through the tube 40, typically by connecting through a suction or vacuum connector 60 at or near the proximal end 44 of the tube. The valve structure 54 may also contain a second port to allow upward passage of exhaled air through the expanded cuff 46. Usually, the second port will comprise a one-way valve structure which will prevent entry of secretions or air from the upper airway past the expandable cuff 46. When the patient exhales with a sufficient pressure, however, air will flow through the second port past the patient's larynx to allow the patient to speak. When using an inflatable cuff 46, an inflation port 62 will usually be provided near the proximal end 44 of the tube 40. The tube 40 will thus usually be a multi-lumen extrusion to provide the necessary flow paths therethrough.

Figure 4A:
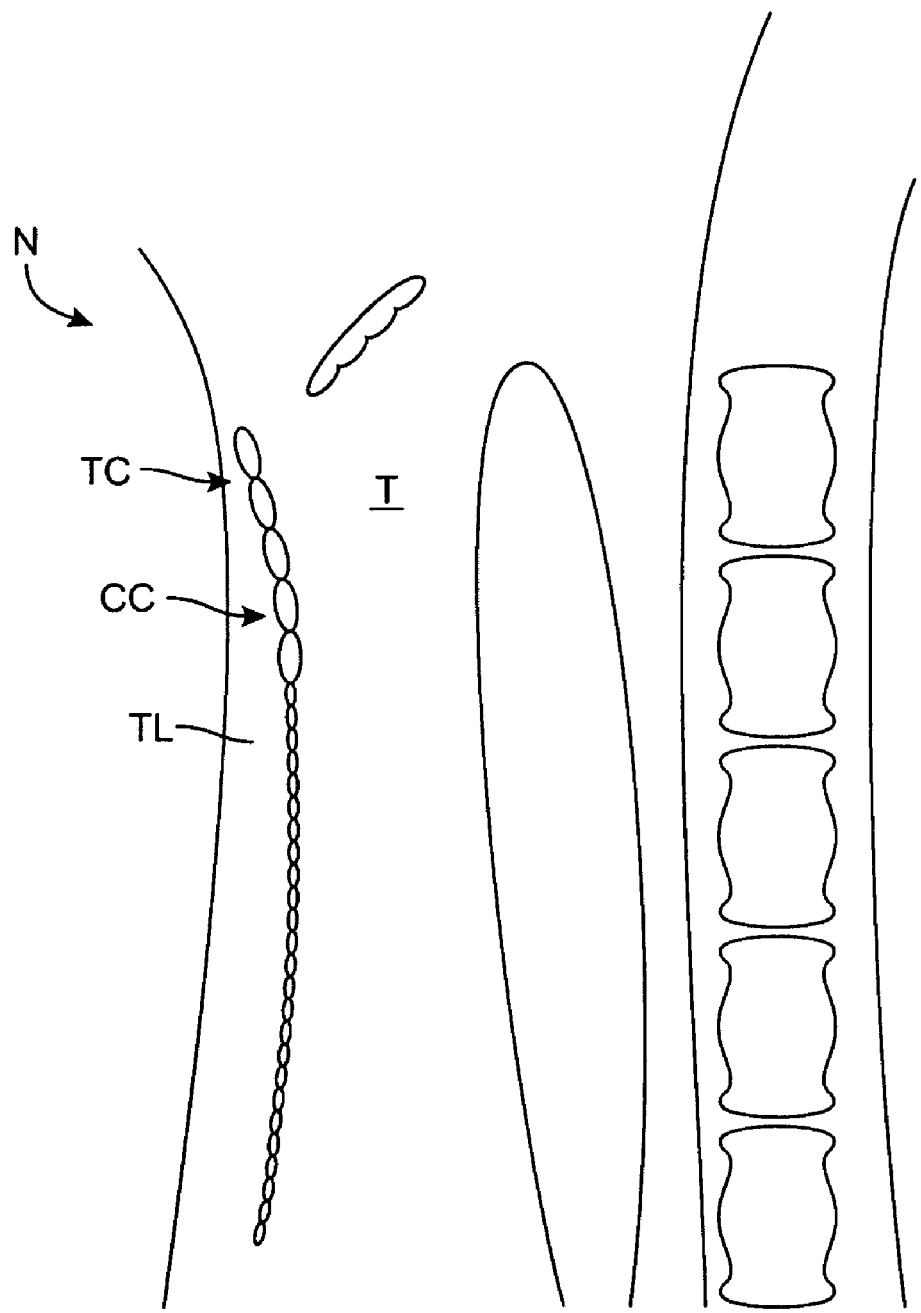
FIGS. 4A-4F illustrate a method of the present invention for deploying the system of FIGS. 2 and 3 in the neck of a patient.

Referring now to FIGS. 4A-4F, deployment and use of the tracheal ventilation system 10 in the trachea of a patient will be described. As shown in FIG. 4A, the trachea T through the patient's neck region N is protected at its upper end by the thyroid cartilage TC and the cricoid cartilage CC at the upper end of the trachea. An incision to perform the tracheostomy is made in the region indicated at TR.

Figure 4B:
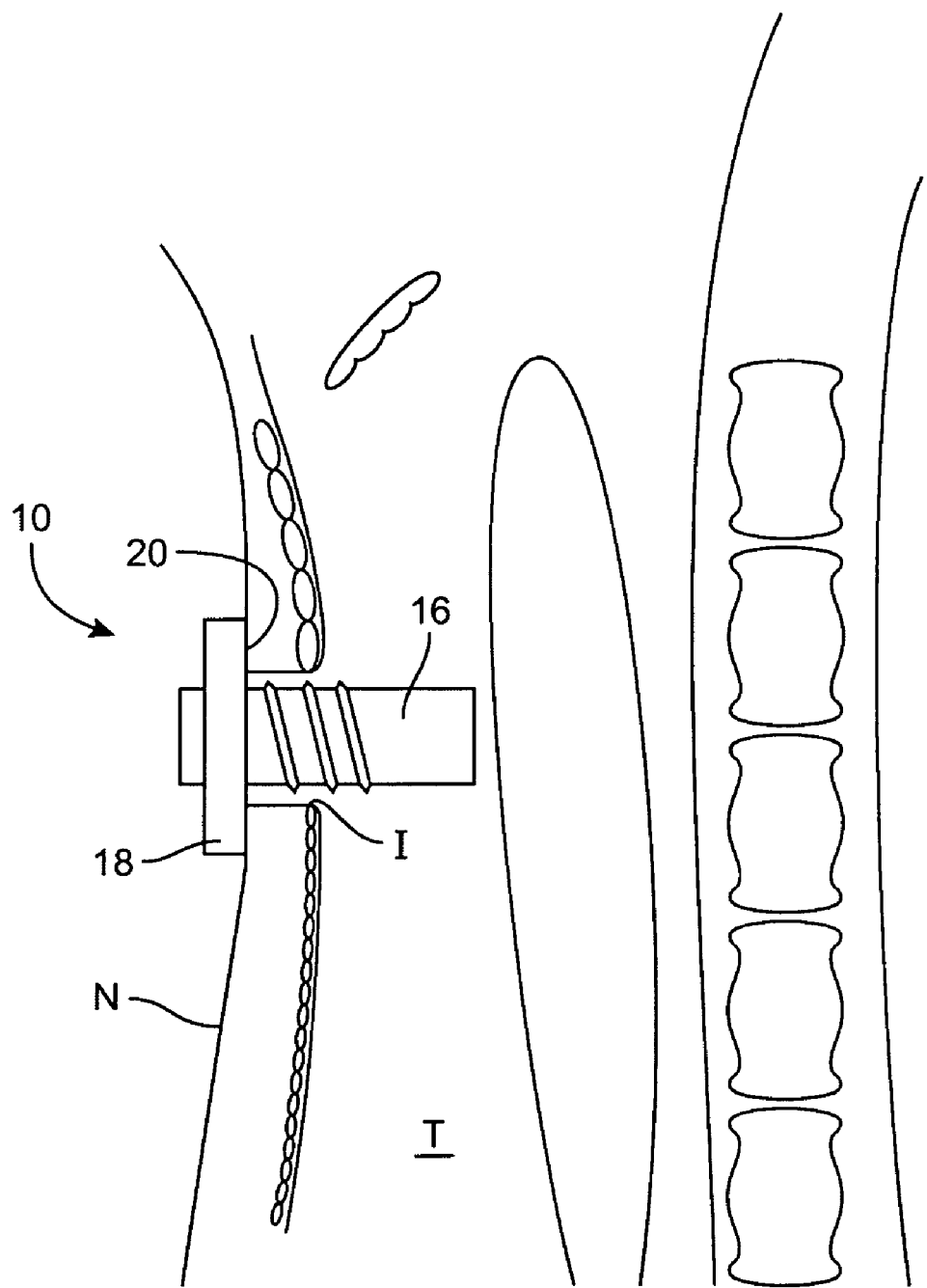
Figure 4C:
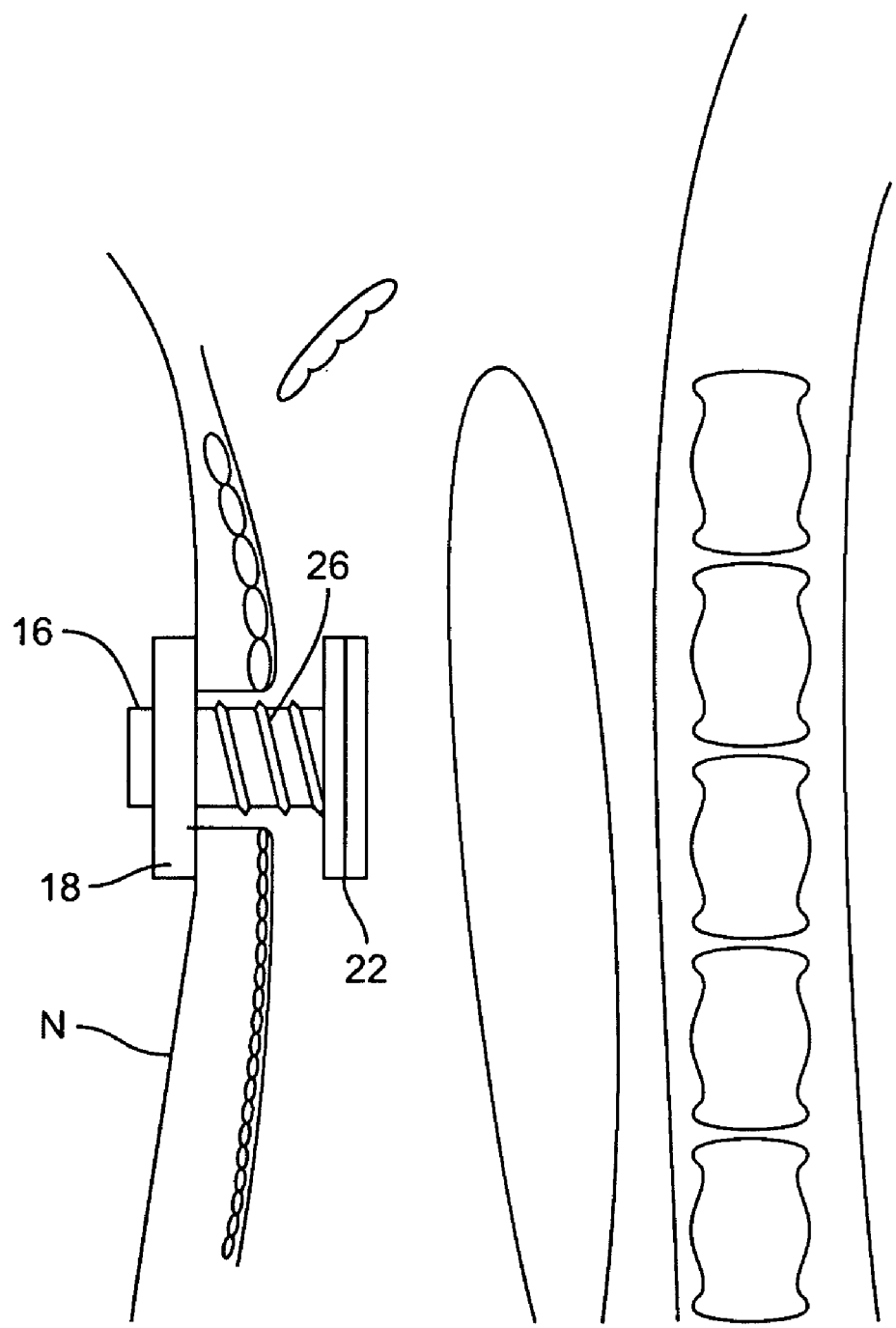
Figure 4D:
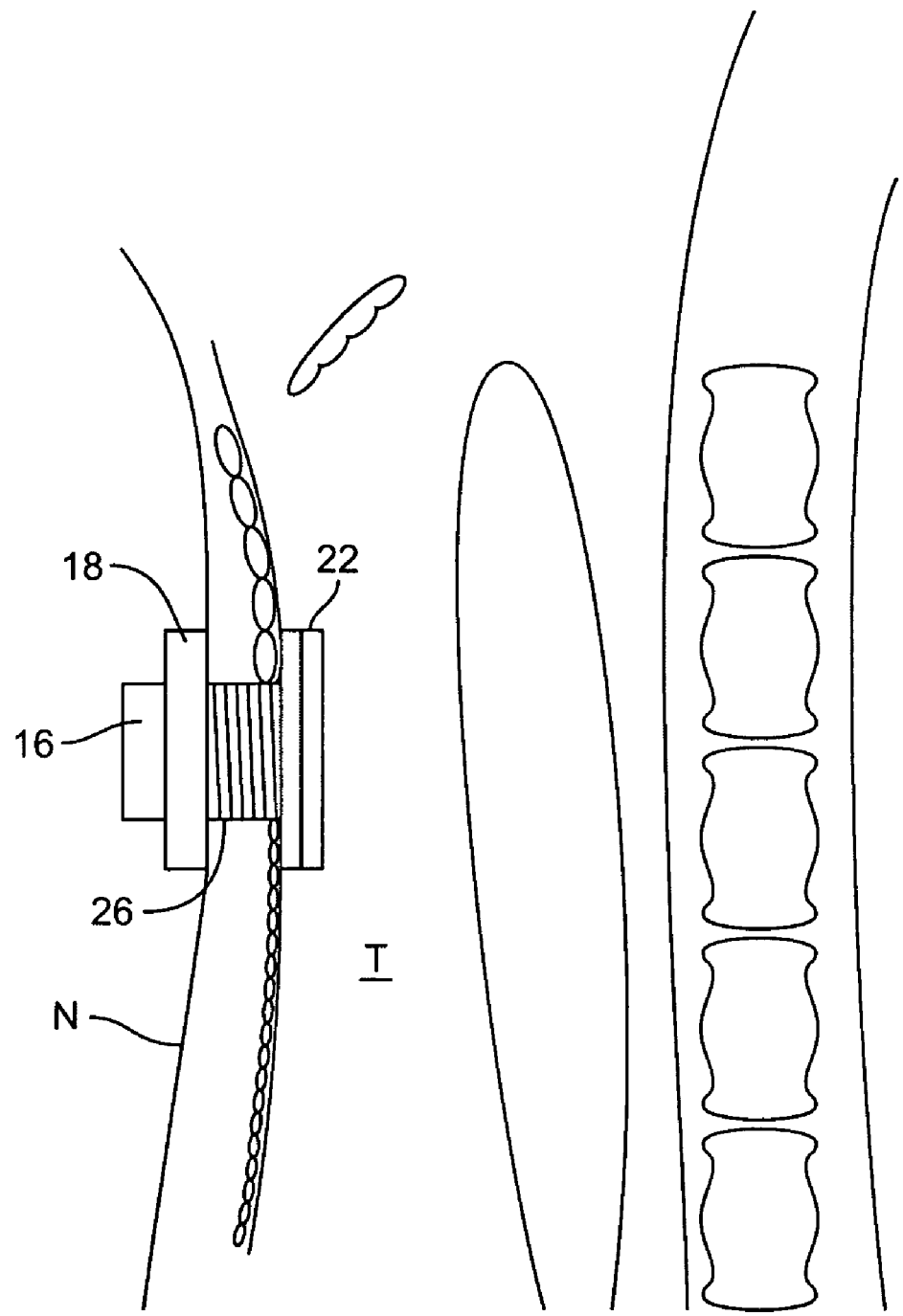

After a surgical incision is made in this region by conventional techniques, the conduit 16 of access device 10 may be inserted through the incision so that the posterior surface 20 of the base 18 is brought against the skin of the neck surrounding the incision, as shown in FIG. 4B. The anchor structure 22 is then radially expanded, as shown in FIG. 4C, and the expanded anchor drawn against the interior surface of the trachea T, as shown in FIG. 4D. Specific mechanisms for deploying the anchor 22, and for shortening the distance between the anchor and the base 18, will be described in detail with respect to certain specific embodiments hereinafter.

Figure 4E:
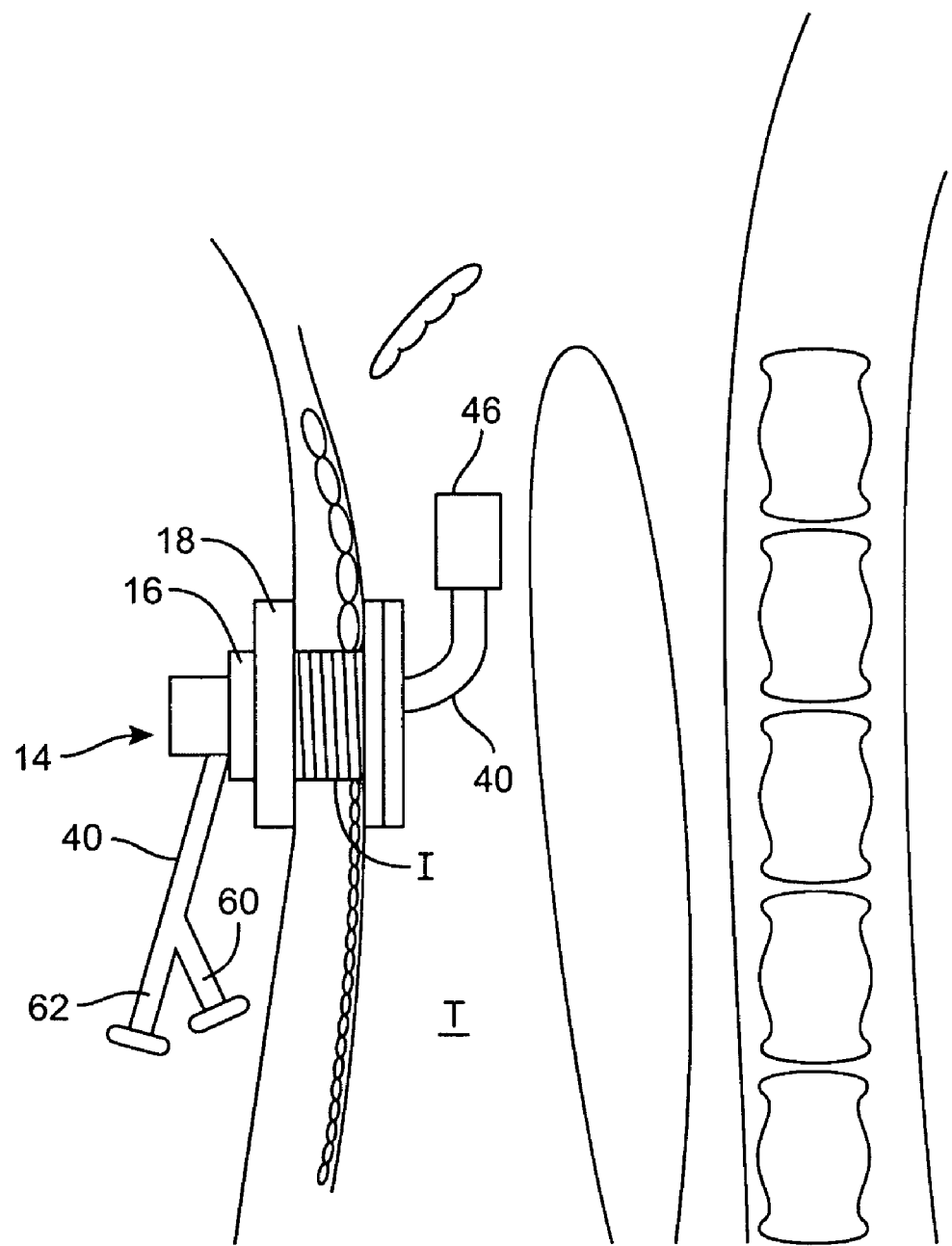
Figure 4F:
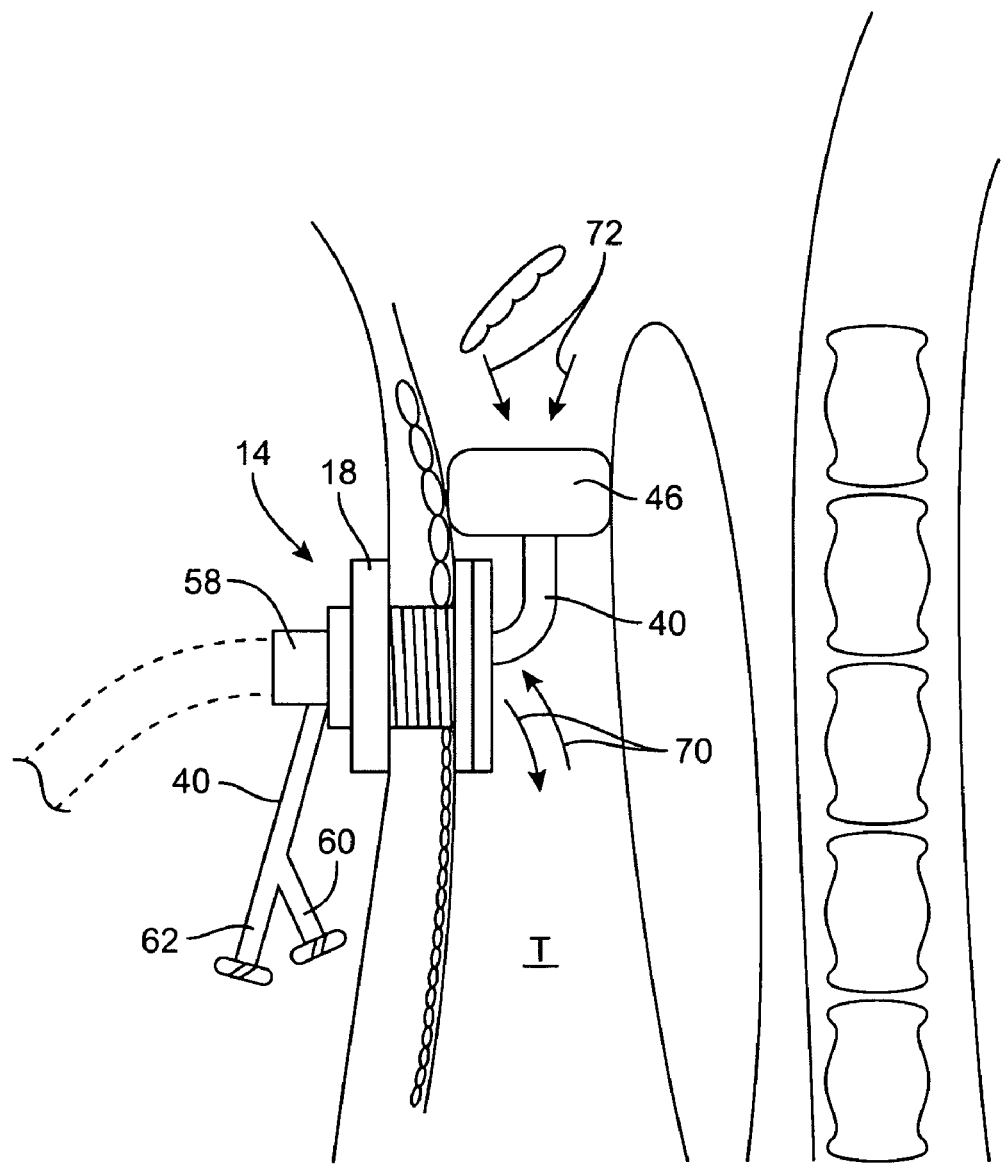

After the anchor is tightened against the inner wall of the trachea T, as shown in FIG. 4D, the ventilation device 14 may be introduced through the passageway defined through conduit 16, as shown in FIG. 4E. The ventilation device is introduced with the expandable cuff 46 in its unexpanded, low-profile configuration. The cuff 46 will be deployed upwardly in the trachea so that it is disposed above the incision I after the device 14 is in place. The cuff 46 may be expanded, typically by inflating through inflation port 62, as shown in FIG. 4F, and a ventilation device may be connected to the ventilation tube 58 as shown in broken line in FIG. 4F. Once in place, air may pass through the ventilation fitting 58, as shown by arrows 70, and the expanded cuff 46 will collect secretions passing into the trachea, as shown by arrows 72. The ventilation device 14 is held securely in place by the access device, but may be conveniently removed, cleaned, and optionally replaced as required over time. When the ventilation device 14 is removed, however, the access device 10 will generally be left in place. By leaving the access device in place, the tracheal opening is protected and patient trauma significantly reduced. Additionally, reintroduction and/or exchange of the ventilation devices is simplified.

Figure 6A:
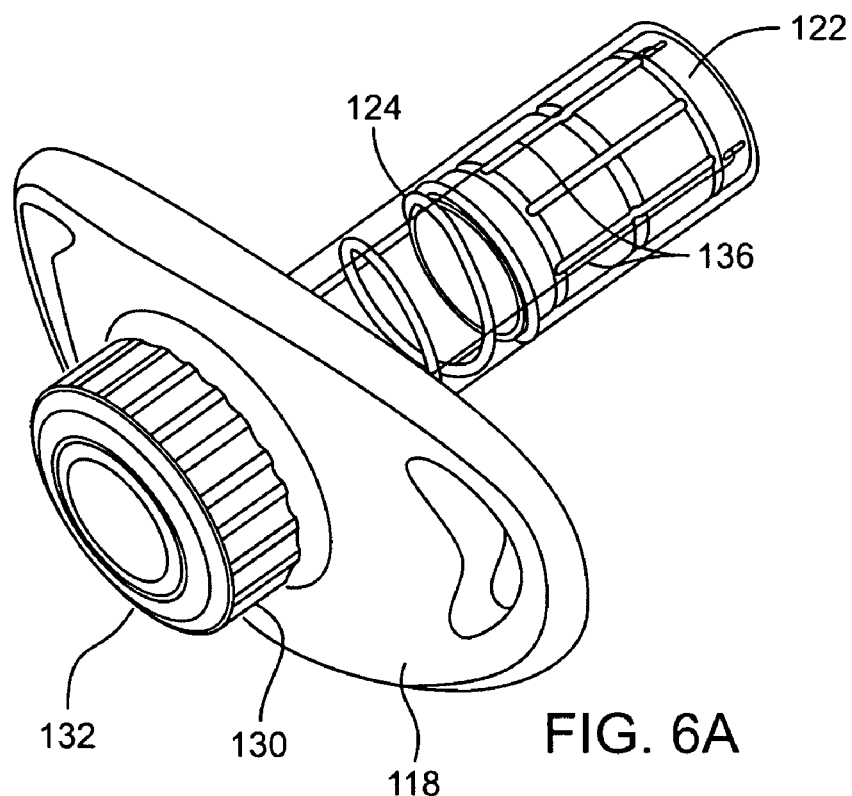
FIGS. 6A and 6B illustrate the access device of FIG. 5 shown with its anchor undeployed (FIG. 6A) and its anchor deployed (FIG. 6B).
Figure 6B:
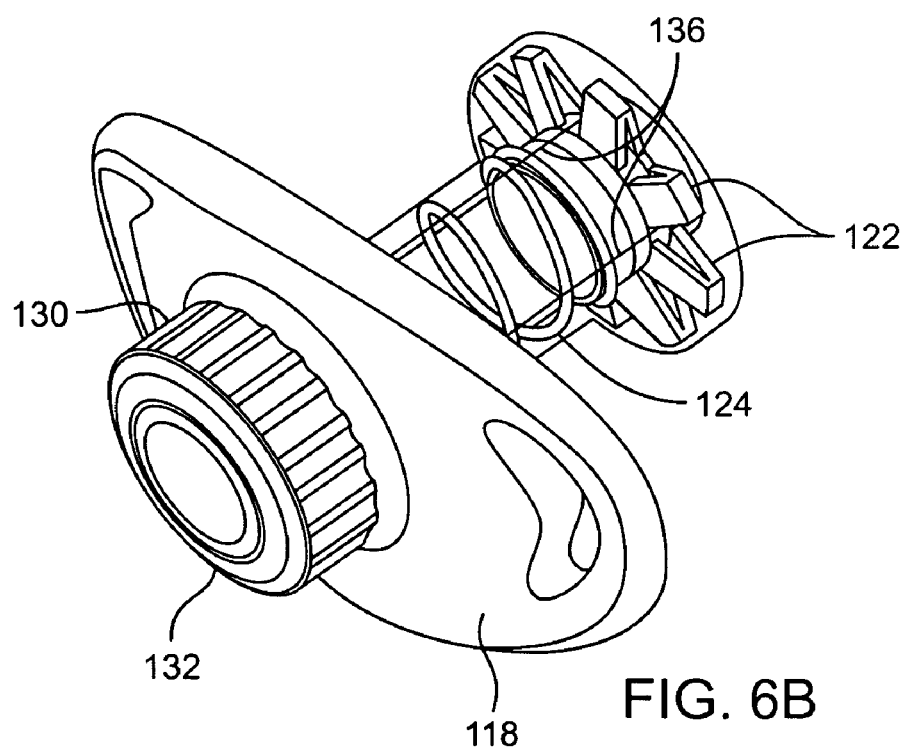

Referring now to FIGS. 5, 6A, and 6B, a detailed construction of the tracheal access system 110 will be described. The detailed system 110 comprises a base plate 118, a conduit 116, an anchor 122, and a coil spring 124. A flexible outer sheath 126 is provided to cover the anchor 122 and compression spring 124, as shown in more detail in FIG. 6A. A rotatable control ring 130 mounts on the forward end of the conduit 116, and is secured by a flange 132 and lock washer 134. Four tethers 136 are provided, and extend between a posterior end 140 of the anchor 122 and the control ring 130. The control ring may be rotated and may act as a reel in order to draw in the tethers in order to shorten and deploy the anchor, in the form of an expansible malecot, as best shown in FIG. 6B. After the malecot anchor 122 has been deployed, the control ring may be further rotated in order to draw the expanded anchor toward the base plate 118 in order to tighten the access device in the tissue opening through which it has been introduced.

Figure 7:
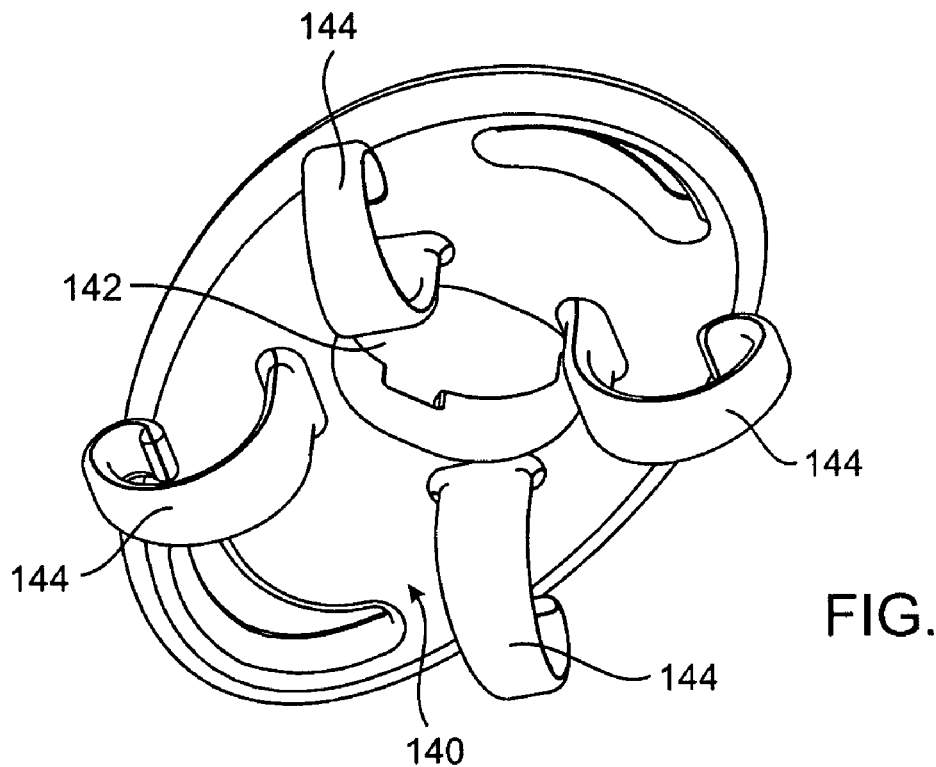
FIG. 7 illustrates a base of a second exemplary access device having a plurality of hooks utilized as the anchor.
Figure 8:
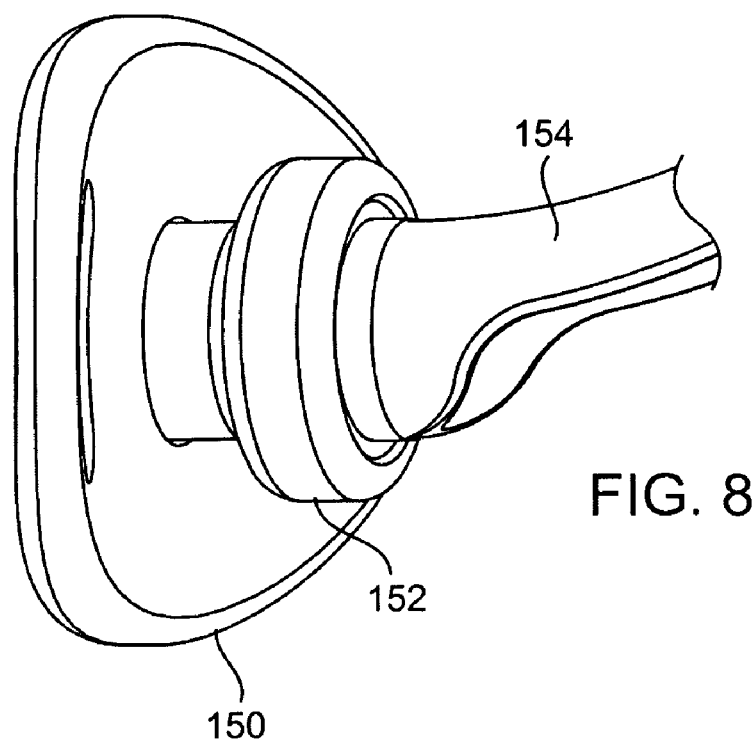
FIG. 8 illustrates a further alternative embodiment of the access device of the present invention illustrating an inflatable balloon as the anchor device.

While the anchor mechanism illustrated in FIGS. 5, 6A, and 6B will often be preferred, alternative anchor mechanisms for holding the base plate within the tissue opening may also be provided. For example, as shown in FIG. 7, a base plate 140 having an aperture 142 for receiving a conduit (not shown), may comprise deployable hook elements 144 for securing the plate over a tissue opening. For example, the hooks may be resilient and may be straightened prior to introduction through the tissue opening. Once in place, the hook constraint my be removed, allowing the hooks to curl back and deploy against the posterior side of the tissue. As shown in FIG. 8, a base 150 may be provided with an inflatable anchor 152 formed over a conduit 154. A lumen (not illustrated) may be provided in the conduit for inflating the balloon.

Figure 9:
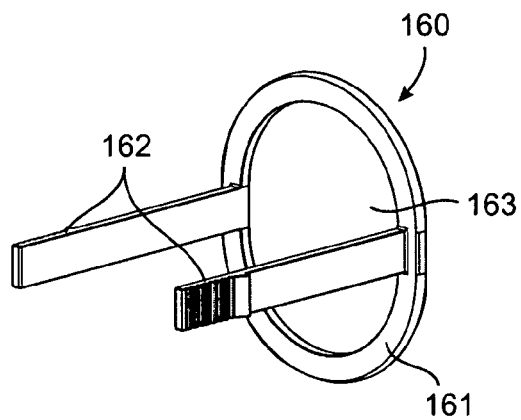
FIGS. 9-11 illustrate yet a further embodiment of the access device of the present invention illustrating use of a locking clip to deploy an anchor.
Figure 10:
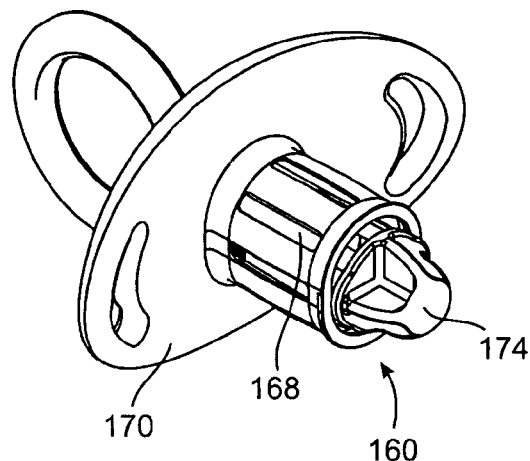
Figure 11:
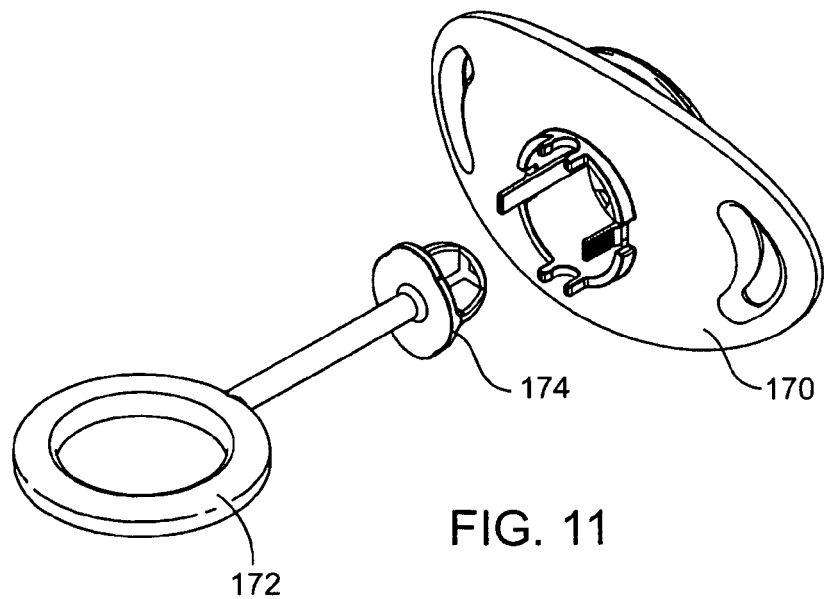

An alternative locking mechanism for a radially expansible malecot anchor is illustrated in FIGS. 9-11. A locking clip 160 (FIG. 9) comprises a pair of resilient fingers 162, each having a ratchet surface 164 near a distal end thereof. A locking clip 160 may be placed with the fingers 164 disposed within a radially expandable malecot 168 on the posterior surface of a base 170, as illustrated in FIG. 10. A pull tool 172 (FIG. 11) may be inserted through the malecot 168 so that a distal puller 174 can be engaged against the ring 161 of the locking clip 160. The ring has an oval opening 163 which permits entry of the oval puller 164 when properly aligned. By then rotating the puller 174 90°, the puller will engage the narrow diameter of the ring 161 to allow the malecot to be actually shortened and radially expanded. The malecot will be held in its radially expanded position by engagement of the ratchet surface 164 against the base 170, as best seen in FIG. 11.

Figure 12:
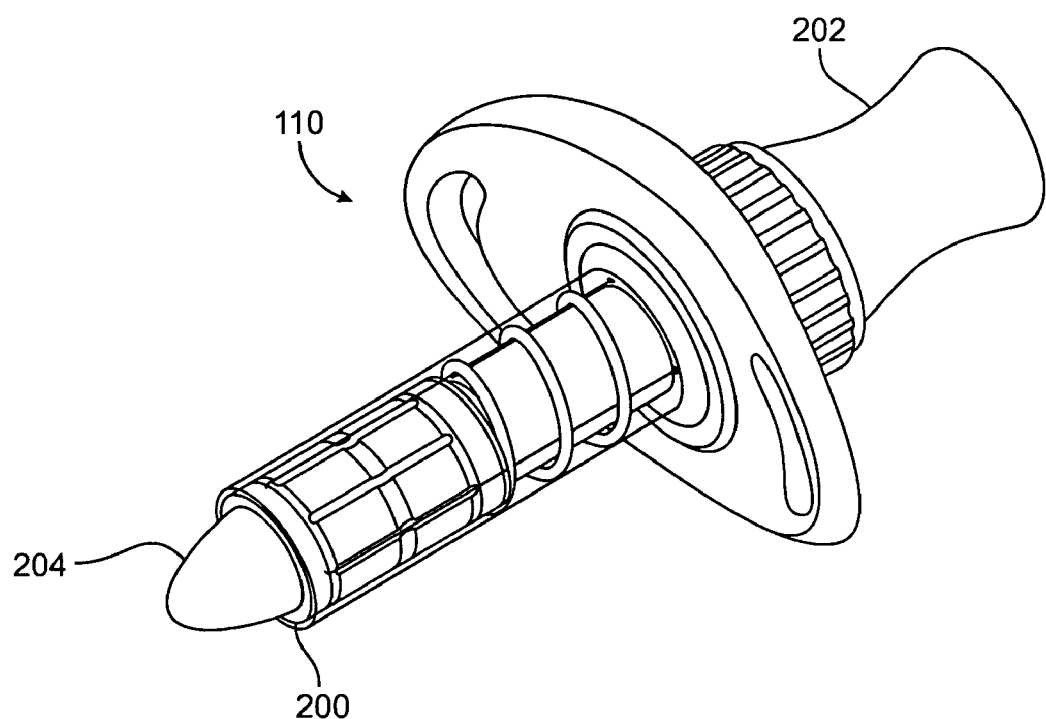
FIG. 12 illustrates use of a straight obturator which can be used with the access device of the present application for deployment.
Figure 13:
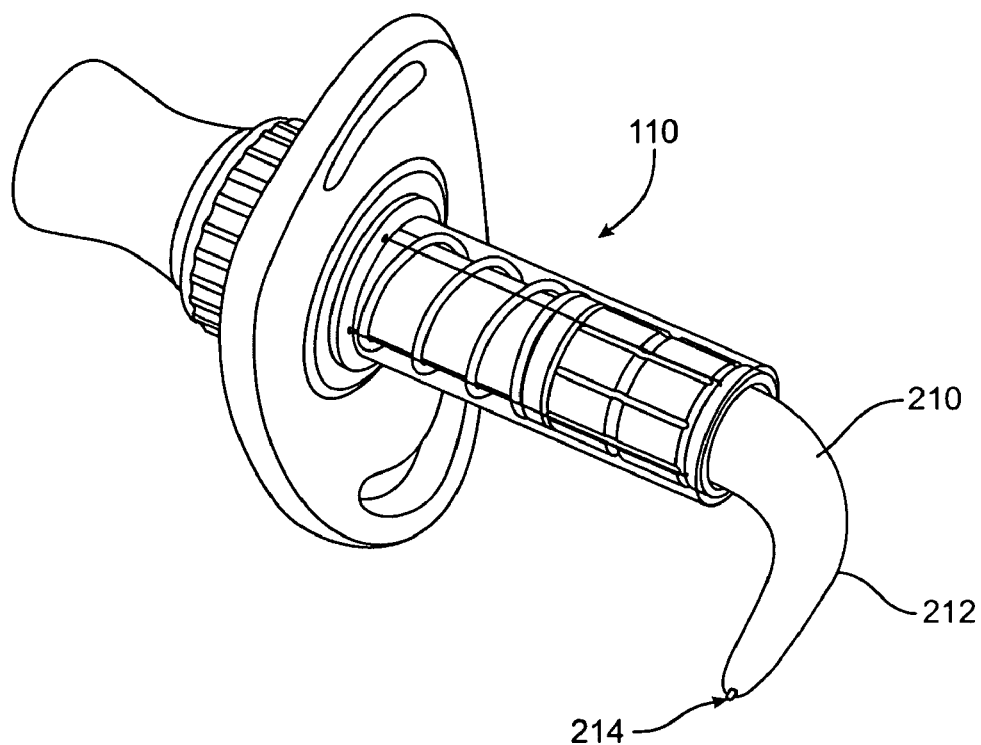
FIG. 13 illustrates an obturator having a bent tip which can be used with a guidewire for introducing the access device of the present invention.

Referring now to FIGS. 12 and 13, obturators may be used to facilitate introduction of the access devices through the stomal openings in the trachea or other body surfaces. For example, a straight obturator 200 may be placed through the central opening of the access device 110, as shown in FIG. 12. Conveniently, a handle 202 will be provided on the proximal end of the obturator 200, and a blunt tip 204 will be provided on the distal end of the obturator. An obturator 210, as illustrated in FIG. 13, has a deflected distal tip 212 and a guidewire lumen therethrough 214. Thus, the obturator 210 can be used for introducing an access device 110 over a guidewire.

Figure 14:
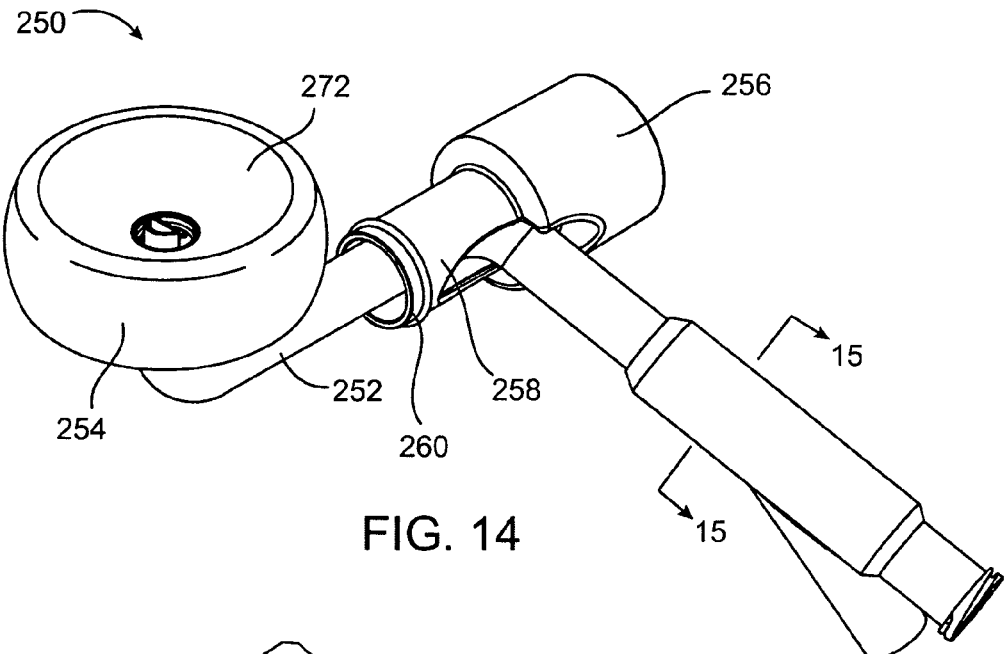
FIG. 14 is a detailed illustration of a first embodiment of the tracheal ventilation device of the present invention.
Figure 15:
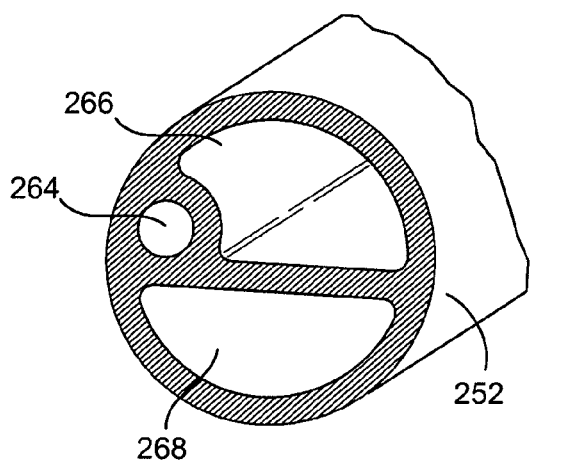
FIG. 15 is a cross-sectional view taken along line 15-15 of FIG. 14.
Figure 16:
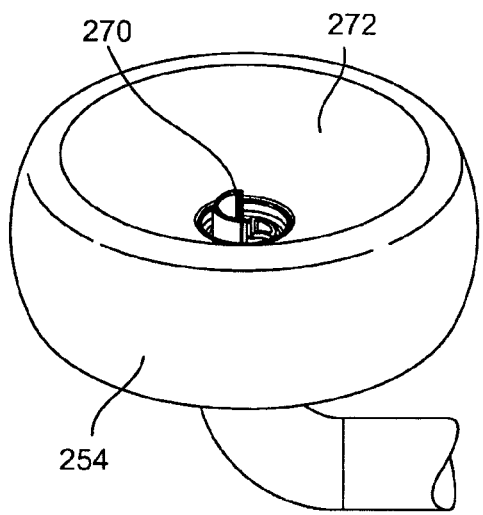
FIG. 16 is an enlarged view of the expandable cuff of the ventilation device of FIG. 14.

Referring now to FIGS. 14-16, an exemplary ventilation device 250 comprises a tube 252, an inflatable cuff 254, and a ventilation fitting 256. The ventilation fitting has a distal end 258 adapted to fit in the central passage of an access device, such as the central lumen of device 110. An O ring 260 provides a hermetic seal when the fitting 256 is within the interior conduit 116. The tube 252 is typically a three-lumen extrusion, including a balloon inflation lumen 264, an aspiration lumen 266, and a ventilation lumen 268. The aspiration lumen is connected to an open port 270 disposed within the inflatable cuff 254, as best seen FIG. 16. The open port 270 allows removal of secretions which collect within a concave depression or other concavity in an upper surface of the cuff 254. A second valve 274 is provided adjacent the aspiration port 270, and typically includes a one-way valve structure permitting air to flow from beneath the cuff 254 to above the cuff. In this way, the patient may exhale and permit to pass upward through the valve 274 to enter the region of the larynx to permit speech. In particular, by covering the ventilation fitting 256 (optionally having removed any ventilator device), the air will have no other place to go, thus will all pass through the valve 274 into the larynx. After the patient is done speaking, the ventilator may be uncovered and/or the ventilation device may be reconnected.

Figure 17:
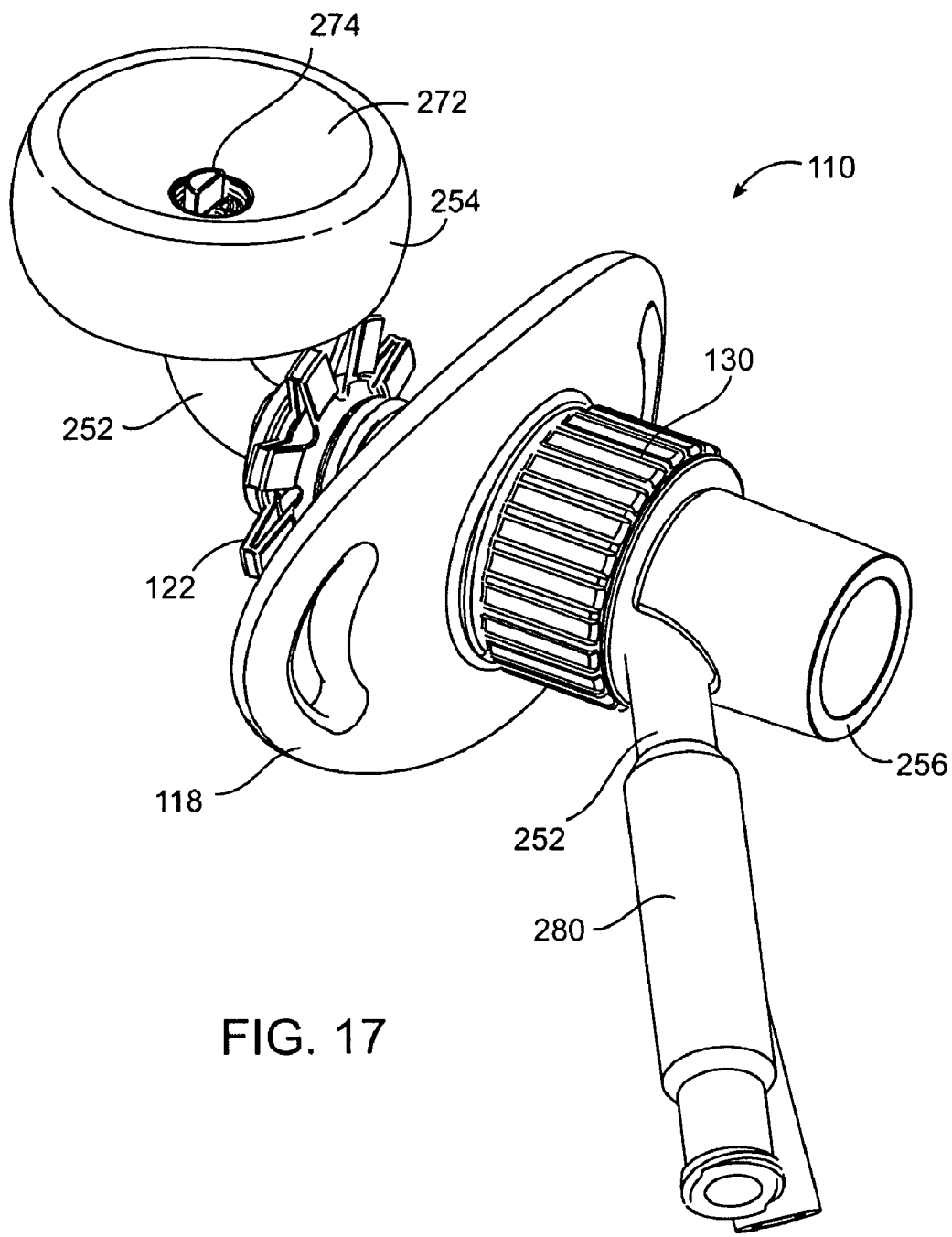
FIG. 17 illustrates the ventilation device of FIG. 14 present in the access device of FIGS. 2 and 3.

As shown in FIG. 17, the ventilator fitting 256 may be introduced through the center of the control ring 130 and the access device 110. A Y-connector at the proximal end of tube 252 provides for both aspiration (through aspiration lumen 266) and balloon inflation (through inflation lumen 264).

Figure 18:
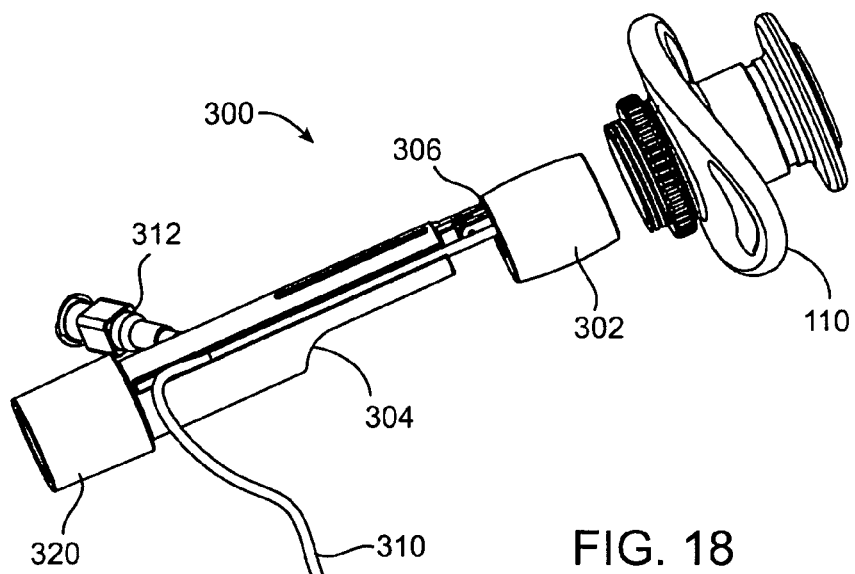
FIGS. 18-20 illustrate a second embodiment of a ventilation device according to the present invention being deployed through an access device.
Figure 19:
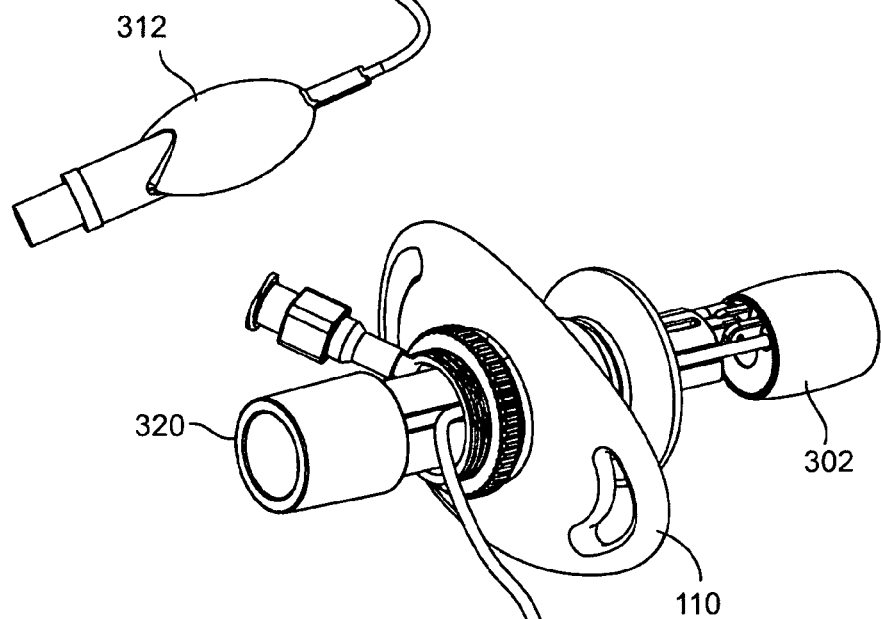
Figure 20:
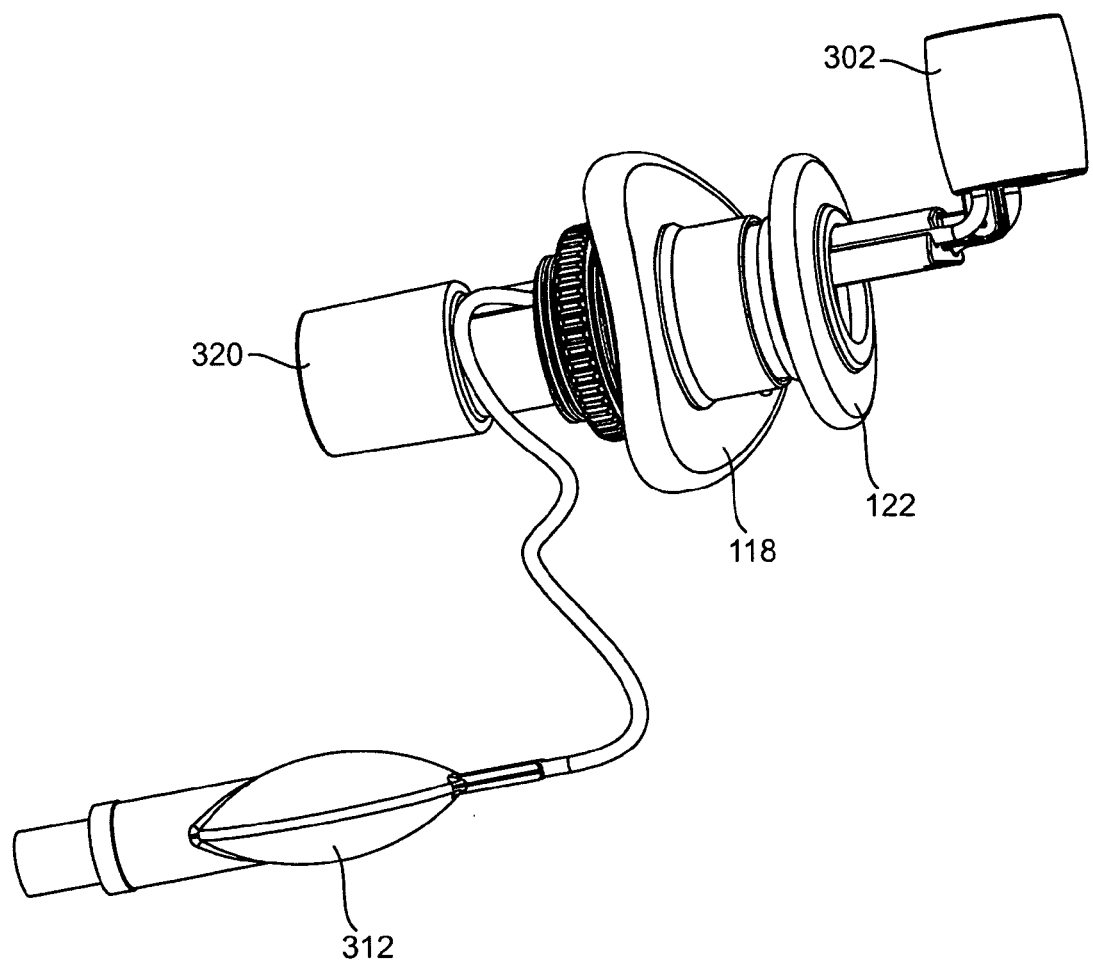

Referring now to FIGS. 18-20, an alternative ventilator device 300 for introduction through an access device 110 is illustrated. The ventilation device 300 includes an expandable cuff 302 which is connected to a tube 304 by a hinge structure 306. A cuff inflation tube 310 is connected to a hand pump 312 at one end and to the cuff 302 at the other end. An aspiration connection 312 is similarly connected through a flexible tube to a valve within the interior of the cuff 302 (not shown).

The expandable cuff 302 may be introduced through the central passage of the access device 110 while in axial alignment with the tube 304, as shown in FIG. 18. After the cuff 302 has been fully inserted through the access device 110, as shown in FIG. 19, the cuff may then be turned upwardly at a generally right angle as shown in FIG. 20. The cuff 302 may then be inflated using the pump 312. Ventilation fitting 320 remains available for patient breathing and optional connection to a ventilator.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A percutaneous access device, said device comprising:
a base having a posterior surface adapted to cover a percutaneous tissue penetration;
a conduit having an access lumen disposed through the base and adapted to pass through the penetration; and
an anchor on a posterior portion of the conduit, said anchor shiftable between an expanded anchoring configuration and an unexpanded deployment configuration, wherein the anchor comprises:
an anchor element which radially expands upon axial compression;
a compliant mount securing the anchor element to the base; and
a pulling assembly connected between the anchor element and the base to draw the anchor element toward the base and to both (1) axially compress the anchor element to cause radial expansion and (2) pull the radially expanded anchor element against a posterior tissue surface.

2. A percutaneous access device as in claim 1, wherein the anchor element comprises a malecot or a deformable braid.

3. A percutaneous access device as in claim 1, wherein the compliant mount comprises a coil spring.

4. A percutaneous access device as in claim 1, wherein the pulling assembly comprises a reel on the base, and one or more tethers between the reel and anchor.

5. A percutaneous access device as in claim 1, wherein the pulling assembly comprises coaxial tubes.

6. A percutaneous access device as in claim 1, wherein the pulling assembly comprises a locking clip and a pull tool.

7. A method for providing percutaneous access through skin, said method comprising:
penetrating the skin to provide an access hole;
passing a conduit through the hole so that a posterior surface of a base on the conduit covers the access hole;
expanding an anchor on the conduit over a posterior surface of the skin; and
adjusting the distance between the expanded anchor and the posterior surface of the base to accommodate the thickness of the wall,
wherein adjusting comprises compressing a compliant member between the expanded anchor and the base, and compressing comprises reeling tethers connected between the anchor and the base.

8. A tracheal ventilation device comprising:
a tube having a distal end, a proximal end, and an aspiration lumen therethrough; and
an expandable cuff at a distal end of the tube, said cuff having when expanded a periphery which seals against a tracheal wall and an upper surface adapted to collect and pool nasal secretions, wherein the aspiration lumen is coupled to aspirate the pooled secretions;
wherein a portion of the tube is upwardly bent or bendable so that the cuff is above an axis of the tube when deployed in the trachea,
wherein the tube has at least a second lumen for ventilation, the second lumen connected to a one-way valve on the cuff that permits air flow to the larynx.

9. A tracheal ventilation device as in claim 8, wherein the tube has at least a third lumen for inflating an inflatable expandable cuff.

10. A tracheal ventilation device as in claim 8, wherein the tube is hinged to allow axial alignment of the cuff during deployment and upward orientation of the cuff after entry to the trachea.

11. A tracheal ventilation device as in claim 8, wherein the upper surface of the expandable cuff has a concave region for collecting and pooling the nasal secretions.

12. A tracheal ventilation device as in claim 11, wherein the upper surface of the cuff has a conical concavity.

13. A tracheal ventilation device as in claim 8, wherein the expandable cuff is inflatable.

14. A tracheal ventilation device as in claim 8, wherein the expandable cuff is self-expanding.

15. A tracheal ventilation device comprising:
a tube having a distal end, a proximal end, and an aspiration lumen therethrough;
an expandable cuff at the distal end of the tube, said cuff having when expanded a periphery which seals against a tracheal wall and an upper surface adapted to collect and pool nasal secretions, wherein the aspiration lumen is coupled to aspirate the pooled secretions; and
a one-way valve in the cuff to permit air from the lungs to pass upwardly into the larynx when the cuff is expanded in the trachea.

16. A tracheal ventilation device as in claim 15, wherein the tube has at least a second lumen for ventilation.

17. A tracheal ventilation device as in claim 16, wherein the tube has at least a third lumen for inflating an inflatable expandable cuff.

18. A tracheal ventilation device as in claim 16, wherein the second lumen is connected to a one-way valve in the cuff that permits air flow to the larynx.

19. A tracheal ventilation device as in claim 15, wherein the tube is hinged to allow axial alignment of the cuff during deployment and upward orientation of the cuff after entry to the trachea.

20. A tracheal ventilation device as in claim 15, wherein the upper surface has a concave region for collecting and pooling the nasal secretions.

21. A tracheal ventilation device as in claim 20, wherein the upper surface of the cuff has a conical concavity.

22. A tracheal ventilation device as in claim 15, wherein the expandable cuff is self-expanding.

23. A tracheal ventilation device comprising:
   a tube having a distal end, a proximal end, and an aspiration lumen therethrough, wherein the tube includes at least a first lumen to permit air flow to the larynx when deployed in the trachea, at least a second lumen connected to a one-way valve in the cuff that permits air flow to the larynx for ventilation, and at least a third lumen for inflating an inflatable expandable cuff;
   an expandable cuff at a distal end of the tube, said cuff having when expanded a periphery which seals against a tracheal wall and an upper surface adapted to collect and pool nasal secretions, wherein the aspiration lumen is coupled to aspirate the pooled secretions; and
   a ventilator fitting having a first end adapted to removably mount in a tracheal access device, a second end proximal to the first end and adapted to removably connect to a ventilator, and a passage therethrough to receive the tube.

24. A tracheal ventilation device as in claim 23, wherein the tube is hinged to allow axial alignment of the cuff during deployment and upward orientation of the cuff after entry to the trachea.

25. A tracheal ventilation device as in claim 23, wherein an upper surface of the expandable cuff has a concave region for collecting and pooling the nasal secretions.

26. A tracheal device as in claim 25, wherein the upper surface of the cuff has a conical concavity.

27. A tracheal ventilation device as in claim 23, wherein the expandable cuff is inflatable.

28. A tracheal ventilation device as in claim 23, wherein the expandable cuff is self-expanding.

29. A method for providing tracheal ventilation, said method comprising:
   forming a percutaneous hole into a patient's trachea;
   introducing a tracheal ventilation device through the hole;
   expanding a cuff on the ventilation device to isolate the trachea below the cuff, wherein the trachea below the cuff is otherwise unblocked to permit air exchange through the cuff on the ventilation device and air flow up to the larynx; and
   aspirating collected nasal secretions from a collection location on an upper surface of the cuff.

30. A method as in claim 29, wherein the cuff is expanded within the trachea at a position above the percutaneous hole.

31. A method as in claim 29, wherein the nasal secretions pool in a concavity in an upper surface of the cuff from where they are aspirated.

32. A method as in claim 31, wherein the nasal secretions are aspirated through a vertical passage through the expanded cuff.

33. A method as in claim 29, further comprising anchoring an access device through the percutaneous hole, wherein the tracheal ventilation device is removably introduced through an access passage of the access device.

34. A method for providing tracheal ventilation, said method comprising:
   forming a percutaneous hole into a patient's trachea;
   anchoring an access device in the percutaneous hole, wherein the access device comprises a base and an anchor;
   removably introducing a tracheal ventilation device through an access passage of the access device;
   expanding a cuff on the tracheal ventilation device; and
   aspirating nasal secretions from a collection location on an upper surface of the cuff;
   wherein the anchored access device is adapted to anchor in a hole in the trachea by the base of the anchored access device being secured against the skin and by the anchor of the anchored access device being secured against the inner tracheal wall circumscribing the hole and wherein the trachea below the cuff remains otherwise unblocked to permit air exchange through the ventilation device.

35. A method as in claim 34, further comprising removably introducing a ventilation fitting in the access passage of the access device, wherein the tracheal ventilation device is positioned through.

36. A tracheal ventilation device comprising:
   a tube having a distal end, a proximal end, and an aspiration lumen therethrough;
   an expandable cuff at a distal end of the tube, said cuff having when expanded a periphery which seals against a tracheal wall and an upper surface adapted to collect and pool nasal secretions, wherein the aspiration lumen is coupled to aspirate the pooled secretions; and
   a ventilator fitting having a first end adapted to removably mount in a tracheal access device, a second end proximal to the first end and adapted to removably connect to a ventilator, and a passage therethrough to receive the tube,
   wherein the tube has at least a second lumen for ventilation, and
   wherein the second lumen is connected to a one-way valve in the cuff that permits air flow to the larynx.

\* \* \* \* \*